United States Patent
Iwamoto et al.

(10) Patent No.: US 8,674,319 B2
(45) Date of Patent: Mar. 18, 2014

(54) BEAM MONITOR SYSTEM AND PARTICLE BEAM IRRADIATION SYSTEM

(71) Applicant: Hitachi, Ltd., Tokyo (JP)

(72) Inventors: Tomohisa Iwamoto, Hitachi (JP); Yoshihito Hori, Hitachi (JP); Takayoshi Matsushita, Kasumigaura (JP); Kunio Moriyama, Hitachi (JP); Masahiro Tadokoro, Hitachiota (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/776,062

(22) Filed: Feb. 25, 2013

(65) Prior Publication Data

US 2013/0231517 A1 Sep. 5, 2013

(30) Foreign Application Priority Data

Mar. 2, 2012 (JP) ................. 2012-046060

(51) Int. Cl.
  *G21K 5/04* (2006.01)

(52) U.S. Cl.
  USPC ............. 250/397; 250/336.1; 250/396 R; 250/492.1; 250/492.3; 600/1

(58) Field of Classification Search
  USPC ............. 250/336.1, 340, 396 R, 397, 492.1, 250/492.3; 600/1
  See application file for complete search history.

(56) References Cited

U.S. PATENT DOCUMENTS 2,983,841 A * 5/1961 Veith et al. .................... 315/12.1
2010/0187435 A1 * 7/2010 Iseki et al. ..................... 250/398

FOREIGN PATENT DOCUMENTS

JP 2008-175829 A 7/2008

OTHER PUBLICATIONS

Chu et al., "Instrumentation for treatment of cancer using proton and light-ion beams"; Review of Scientific Instruments; Aug. 1993; pp. 2074-2093; vol. 64; No. 8.

* cited by examiner

*Primary Examiner* — Nicole Ippolito
(74) *Attorney, Agent, or Firm* — Mattingly & Malur, PC

(57) ABSTRACT

Disclosed is a beam monitor system in which signals outputted from a plurality of wires are divided in a multi-wire type monitor for measuring a beam profile of a charged particle beam, an identical number of the wires are grouped, the signals of the respective groups are taken out one piece by one piece to be connected with each other, and the number of the pieces, corresponding to a number of the wires belonging to the one group, are put together to be connected to a signal processor storing connection information.

20 Claims, 9 Drawing Sheets

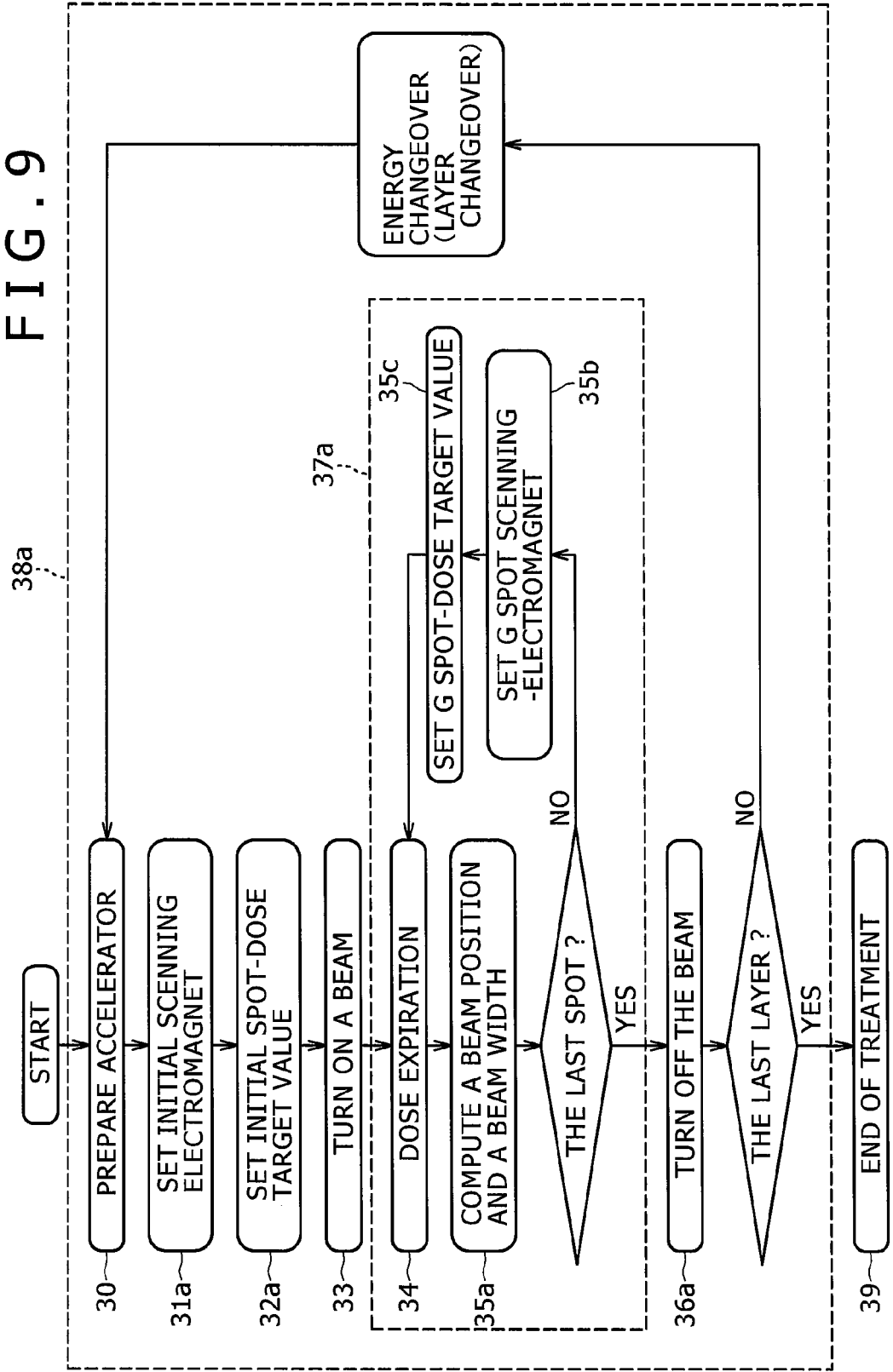

BEAM MONITOR SYSTEM AND PARTICLE BEAM IRRADIATION SYSTEM

FIELD OF THE INVENTION

The present invention relates to a method for monitoring a beam position in a charged particle beam irradiation system, and controlling the beam position, and in particular, to a charged particle beam irradiation system suitable for application to a charged particle beam treatment apparatus for giving treatment to an affected part by irradiating the affected part with a beam of a charged particle such as a proton, a carbon ion, and so forth.

BACKGROUND OF THE INVENTION

There has been known a treatment method whereby an affected part of a patient of cancer, and so forth is irradiated with a charged particle beam (an ion beam) of a proton, a carbon ion, and so forth. A charged particle beam irradiation system (a particle beam emitting apparatus, or a charged particle beam emitting apparatus) for use in this treatment is provided with a charged particle beam generation unit, and a charged particle beam accelerated by the charged particle beam generation unit reaches an irradiation unit provided at a rotary gantry via a first transport system, and a second transport system provided at the rotary gantry, whereupon the charged particle beam emitted from the irradiation unit to irradiate the affected part of a patient. A double scatterer method (Non-patent Document 1, p. 2081, FIG. 35) whereby a beam is expanded by use of a scatterer to be subsequently cut out so as to match with the shape of an affected part, a wobbler method ((Non-patent Document 1, p. 2084, FIG. 41), and a scanning method ((Non-patent Document 1, pp. 2092 and 2093) for causing a fine beam to scan within an affected part have been known as a beam irradiation method of the irradiation unit.

Attention has been focused on the scanning method among those beam irradiation methods because the scanning method has a feature that an effect on a normal cell is less, and equipment incorporating a nozzle is unnecessary. It is the feature of the scanning method that outputting of a charged particle beam is stopped in response to a dose to an irradiation subject, an irradiation position of the charged particle beam, called a spot, is changed by controlling energy, and a scanning electromagnet, and emission of the charged particle beam is resumed after completion of such a change, thereby irradiating the irradiation subject (the affected part) with the beam so as to match with the shape of the irradiation subject, while sequentially changing over the irradiation position.

[Patent Document 1] Japanese Unexamined Patent Application Publication No. 2008-175829

[Non-patent Document 1] REVIEW OF SCIENTIFIC INSTRUMENTS, Vol. 64, No. 8 (August, 1993), pp. 2074-2093

SUMMARY OF THE INVENTION

With the charged particle beam irradiation system, in order to effect irradiation so as to match with the shape of an affected part, a beam position monitor (hereinafter referred to as a spot position monitor) is installed at a position on the downstream side of a scanning electromagnet, and immediately before a patient as the irradiation subject.

The spot position monitor is provided with a detector (hereinafter referred to as a channel) called as a multi-wire, representing a scheme whereby a quantity of an electric charge generated by passing of a charged particle beam is stored in a capacitor on a channel-by-channel basis to thereby read an induced voltage. As a signal detected by each of the channels is weak, an amplifier is installed on the downstream side of the channel, and the signal detected by the channel is sent out to a signal processor via the amplifier. The signal processor executes processing of a detection signal received, whereupon a beam monitor control unit finds a position passed by the charged particle beam, and a beam width of the charged particle beam on the basis of a processing signal.

Both signal amplifiers, and the signal processors, corresponding to the number of the channels, are required of the spot position monitor. In order to find the position passed by the charged particle beam, and the beam width, it is necessary to execute signal amplification, and signal processing with respect to all the channels, so that there arises a problem that the further the number of the channels is increased, the longer it takes in order to detect the position of the charged particle beam, and the beam width.

To cope with the problem described as above, Patent Document 1 has disclosed a method for measuring a charged particle beam, whereby a scope of the channels for use in computation is restricted on the basis of information on a position passed by the charged particle beam, and a beam width thereof, pre-designated in a bean-monitoring system provided with both signal amplifiers, and signal processors, corresponding to the number of the channels, before execution of the signal processing, thereby enhancing a processing speed. However, in the case of the method for measuring the charged particle beam, described as above, if a multitude of channels are required, the bean-monitoring system alone will become large in scale, and complex in configuration for the reasons of irradiation applied with a fine beam, and so forth, and therefore, a cost becomes high.

It is therefore an object of the invention to provide a bean monitoring system, and a charged particle beam irradiation system, capable of monitoring a position passed by a charged particle beam, and a beam width thereof, in a simple configuration, and making a determination in short time during spot irradiation according to the scanning method.

There is provided a beam monitor system wherein signals outputted from a plurality of wires are divided in a multi-wire type monitor for measuring a beam profile of a charged particle beam, an identical number of the wires are grouped, the signals of the respective groups are taken out one piece by one piece to be connected with each other, and the number of the pieces, corresponding to a number of the wires belonging to the one group, are put together to be connected to a signal processor storing connection information.

According to the present embodiment, channels for use in working, out a position of the charged particle beam, and a beam width are restricted, so that it is possible to construct a monitor system simple in configuration as compared with a monitor system provided with a signal processor corresponding to all the channels.

BRIEF DESCRIPTION OF THE DRAWINGS

FIG. 9 shows a control flow in charged particle beam irradiation according to a raster scanning method.

DETAILED DESCRIPTION OF THE PREFERRED EMBODIMENTS

Figure 1:
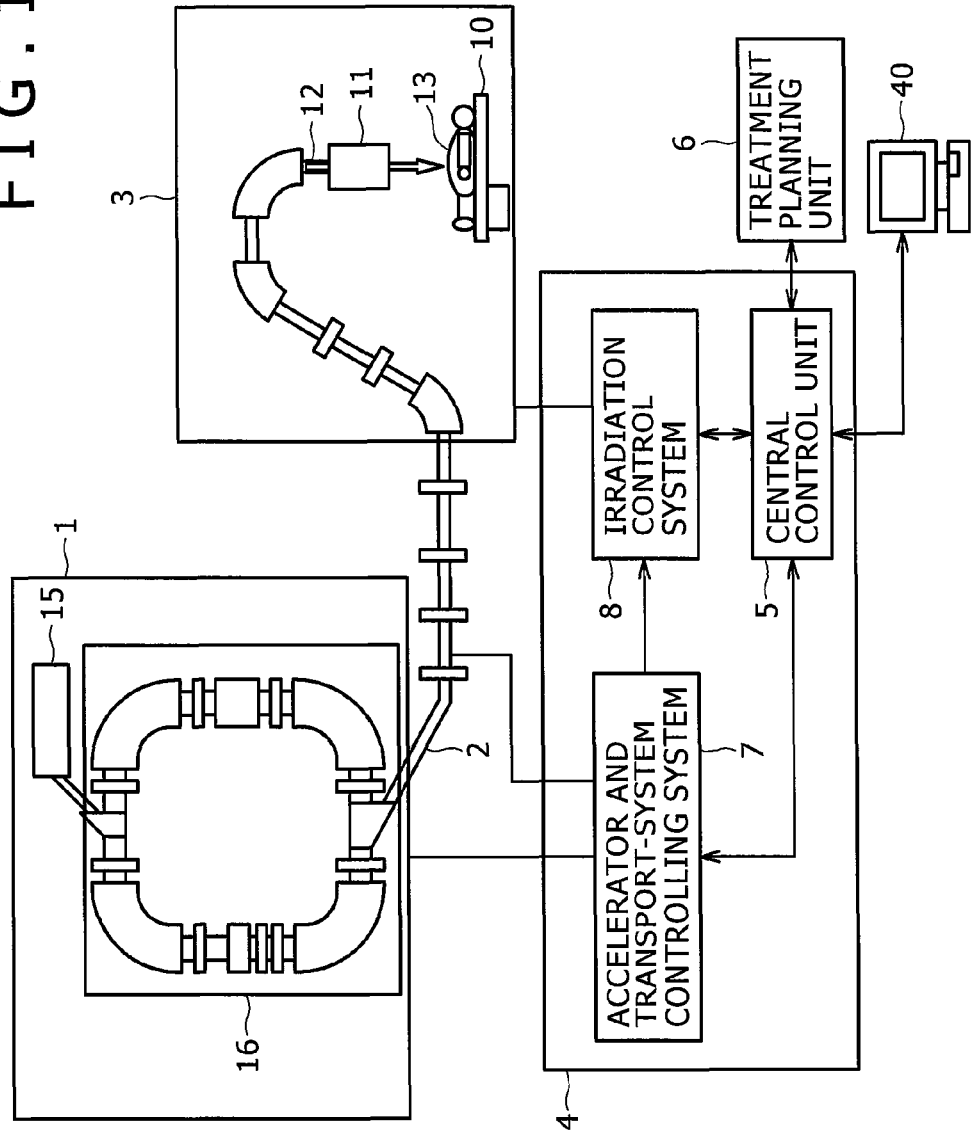
FIG. 1 is a block diagram showing a configuration of a particle beam irradiation system according to one embodiment of to the invention, in whole.

Embodiments of the invention are described hereinafter.

First Embodiment

A preferred embodiment of a particle beam irradiation system according to the invention is described hereinafter with reference to FIGS. 1 and 2. The particle beam irradiation system is a system for irradiating an affected part of a patient fixed on a treatment table (a bed) 10 inside a treatment room with a charged particle beam 12 (for example, a proton beam, a carbon beam, and so forth).

The particle beam irradiation system according to the present embodiment is provided with a charged particle beam generation unit 1, a beam transport system 2, a scanning irradiation unit 3, and a control system 4. The beam transport system 2 connects the charged particle beam generation unit 1 to the scanning irradiation unit 3. The control system 4 is connected to a treatment planning unit 6, and an operation terminal 40, respectively. The operation terminal 40 is provided with an input device where an operator (a treatment worker) inputs data, and an instruction signal, and a display screen.

The charged particle beam generation unit 1 includes an ion source (not shown), a front-stage accelerator 15, and a circular accelerator (synchrotron) 16. In the present embodiment, a synchrotron is described as an example of the circular accelerator 16; however, the circular accelerator 16 may be another accelerator such as a cyclotron, and so forth.

The ion source is connected to a part of the charged particle beam generation unit 1, on the upstream side of the front-stage accelerator 15, and the circular accelerator 16 connected to a part of the charged particle beam generation unit 1, on the downstream side of the front-stage accelerator 15. The beam transport system 2 is connected to a part of the charged particle beam generation unit 1, on the downstream side thereof.

Figure 2:
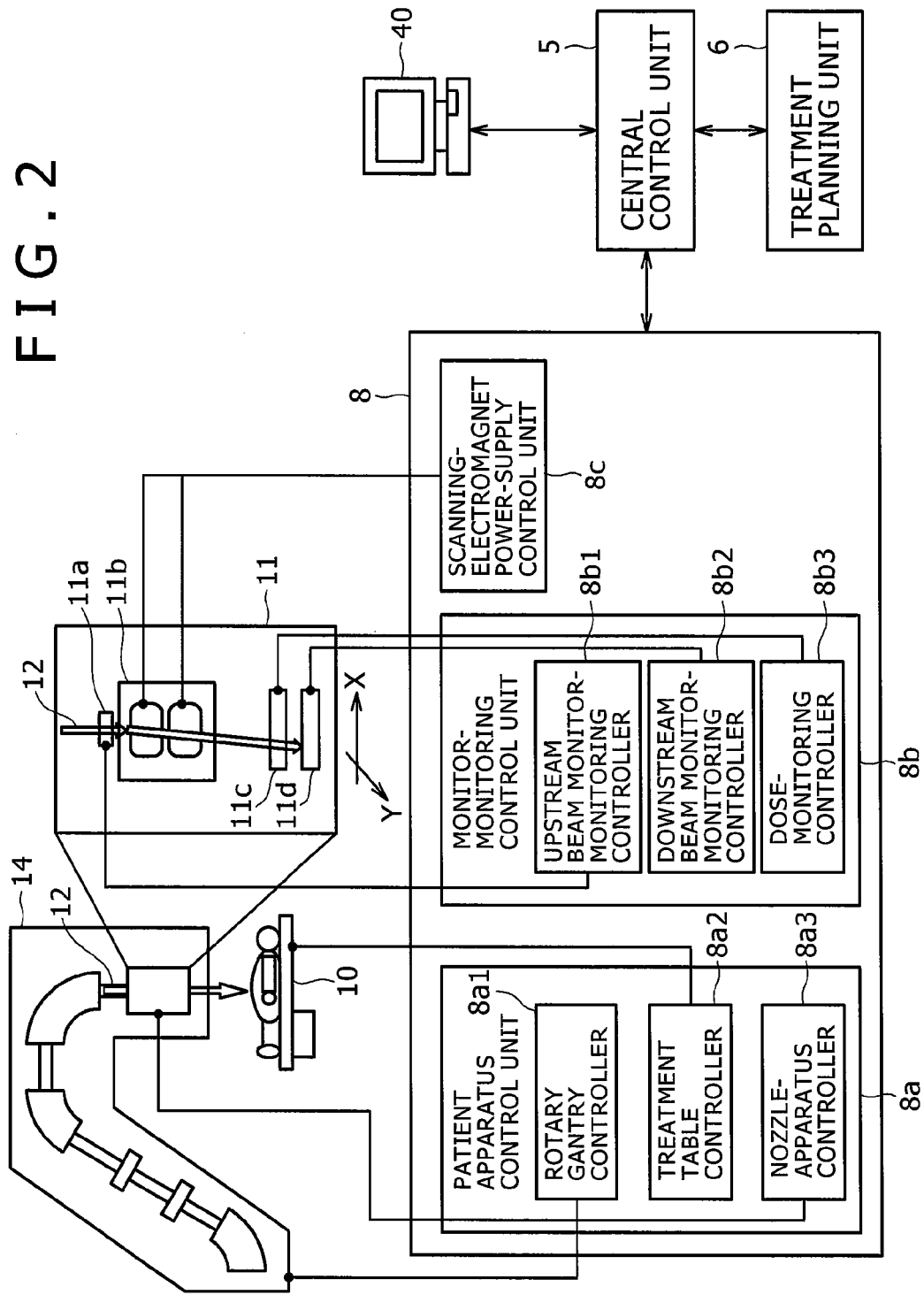
FIG. 2 is a block diagram schematically showing a scanning irradiation unit as well as an irradiation control system of the particle beam irradiation system according to the embodiment of to the invention.

The scanning irradiation unit 3 includes the treatment table 10 on which a patient 13 is placed, an irradiation nozzle (a nozzle device) 11, and a rotary gantry 14, as shown in FIG. 2. The treatment table 10 is disposed inside the treatment room to execute positioning of the patient 13 who is placed thereon. An upstream beam monitor 11a, a scanning electromagnet 11b, a dose-monitor 11c, and a downstream beam monitor 11d are sequentially disposed along a beam path, starting from the upstream side in the travelling direction of the charged particle beam in the irradiation nozzle 11. The upstream beam monitor 11a measures a position passed by a charged particle beam falling into the irradiation nozzle 11, and a beam width (beam diameter) of the charged particle beam. The scanning electromagnet 11b is provided with a first scanning electromagnet for causing a passing charged particle beam to make deflection-scanning in a first direction (for example, in an x-axis direction), and a second scanning electromagnet for causing the passing charged particle beam to make deflection-scanning in a second direction orthogonal to the first direction (for example, in a y-axis direction). Herein, the x-axis direction is one of directions in a plane vertical to the travelling direction of the charged particle beam falling on the irradiation nozzle 11, and the y-axis direction is a direction in the plane, vertical to the x-axis. The downstream beam monitor 11d is installed on the downstream beam side of the scanning electromagnet 11b to measure the position of the passing charged particle beam, and the beam width thereof. More specifically, the downstream beam monitor 11d is a monitor for measuring the position of the charged particle beam, scanned by the scanning electromagnet 11b, and the beam width. The dose-monitor 11c measures a radiation exposure dose of the passing charged particle beam. More specifically, the dose monitor 11c is a monitor for monitoring the radiation exposure dose of the passing charged particle beam that the patient is irradiated with. The rotary gantry 14 is rotatable around Isocentre (not shown). Rotation of the rotary gantry 14 enables an entrance angle of the charged particle beam that the patient 13 is irradiated with.

The control system 4 is provided with a central control unit 5, an accelerator-transport-system controlling system 7, and an irradiation control system 8, as shown in FIG. 1. The central control unit 5 is connected to the treatment planning unit 6, the accelerator-transport-system controlling system 7, the irradiation control system 8, and the operation terminal 40, respectively. The accelerator-transport-system controlling system 7 is connected to the charged particle beam generation unit 1, and the beam transport system 2, respectively, thereby controlling constituent apparatuses thereof. The irradiation control system 8 is connected to the scanning irradiation unit 3, thereby controlling constituent apparatuses thereof.

The irradiation control system 8 is described hereinafter with reference to FIG. 2. The irradiation control system 8 is provided with a patient apparatus control unit 8a, a monitor-monitoring control unit 8b, and a scanning-electromagnet power-supply control unit 8c. The patient apparatus control unit 8a is provided with a rotary gantry controller 8a1 for controlling constituent apparatuses of the rotary gantry 14, a treatment table controller 8a2 for controlling positioning by moving the treatment table 10, and a nozzle-apparatus controller 8a3 for controlling apparatuses disposed inside the nozzle 11. The rotary gantry controller 8a1 controls a rotation angle of the rotary gantry 14, thereby controlling the entrance angle of the charged particle beam that the patient 13 is irradiated with.

The monitor-monitoring control unit 8b is provided with an upstream beam monitor-monitoring controller 8b1 for monitoring, and controlling the upstream beam monitor 11a, a downstream beam monitor-monitoring controller 8b2 for monitoring, and controlling the downstream beam monitor 11*d*, and a dose-monitoring controller 8*b*3 for monitoring, and controlling the dose monitor 11*c*.

The upstream beam monitor-monitoring controller 8*b*1 has a function for measuring the position of the charged particle beam falling into the irradiation nozzle 11, and the beam width of the charged particle beam, and a function for determining whether or not the charged particle beam is abnormal (abnormality-determination processing). The downstream beam monitor-monitoring controller 8*b*2 has a function for measuring the position of the charged particle beam, scanned by the scanning electromagnet 11*b*, and the beam width, and a function for determining whether or not the charged particle beam is abnormal (abnormality-determination processing). More specifically, the functions are described as follows.

The upstream beam monitor-monitoring controller 8*b*1 receives measurement data obtained by the upstream beam monitor 11*a* to execute processing, thereby finding the position passed by the charged particle beam, and the beam width of the charged particle beam. If a beam position obtained is outside a predetermined scope, or the beam Width obtained is outside a predetermined scope, the upstream beam monitor-monitoring controller 8*b*1 determines that the beam is abnormal, thereby outputting an abnormality signal to the central control unit 5. The central control unit 5 outputs a beam-stop command signal to the accelerator-transport system controlling system 7, thereby stopping the charged particle beam outgoing from the charged particle beam generation unit 1. In the present embodiment, a control is made such that the charged particle beam outgoing from the charged particle beam generation unit 1 is stopped. However, a control may be made such that the central control unit 5 controls the beam transport system 2, thereby stopping the charged particle beam falling on the irradiation nozzle 11.

The downstream beam monitor-monitoring controller 8*b*2 receives measurement data obtained by the downstream beam monitor 11*d* to execute processing, thereby finding the position passed by the charged particle beam, and the beam width of the charged particle beam. If a beam position obtained is outside a predetermined scope, or the beam width obtained is outside a predetermined scope, the downstream beam monitor-monitoring controller 8*b*2 determines that the beam is abnormal, thereby outputting an abnormality signal to the central control unit 5. The central control unit 5 outputs a beam-stop command signal to the accelerator-transport system controlling system 7, thereby stopping the charged particle beam outgoing from the charged particle beam generation unit 1. In the present embodiment, a control is made such that the charged particle beam outgoing from the charged particle beam generation unit 1 is stopped. However, a control may be made such that the central control unit 5 controls the beam transport system 2, thereby stopping the charged particle beam falling on the irradiation nozzle 11.

Herein, the beam position of the charged particle beam indicates a position of the center of gravity of the charged particle beam passing through, for example, a beam monitor (the upstream beam position monitor 11*a* or the downstream beam monitor 11*d*). Further, the beam width of the charged particle beam indicates a region of the charged particle beam having passed through the beam monitor, (the upstream beam monitor 11*a* or the downstream beam monitor 11*d*). There are the case of finding the beam width by working out an area of a region where the charged particle beam is detected by the beam monitor (the upstream beam monitor 11*a* or the downstream beam monitor 11*d*) disposed on the plane vertical to the travelling direction of the beam, and the case of finding the beam width by working out the area of a detection region of the charged particle, and a width of the detection region by use of the beam monitor described, and so on.

The scanning-electromagnet power-supply control unit 8*c* controls a power supply (not shown) of the scanning electromagnet 11*b*, thereby controlling an excitation current energizing the scanning electromagnet 11*b*. When an excitation current value of the scanning electromagnet 11*b* is changed, a change occurs to an irradiation position of the charged particle beam toward the patient 13.

Figure 4:
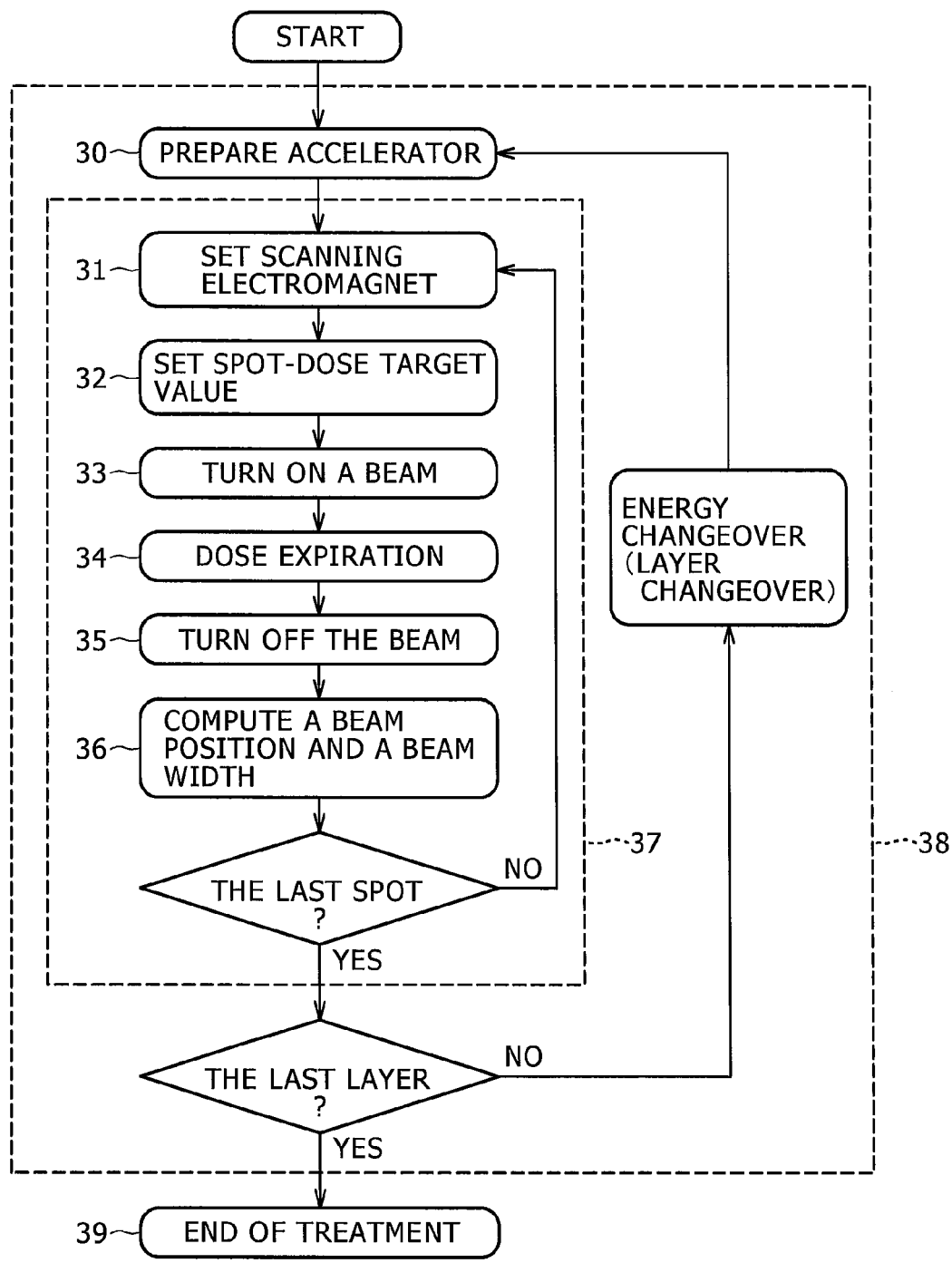
FIG. 4 shows a control flow in charged particle beam irradiation according to the scanning irradiation method.

Next, there is described a flow of treatment from a start of treatment applied to a patient up to treatment completion with reference to FIG. 4. In the present embodiment, there is described a spot-scanning irradiation method whereby an affected part of the patient 13 is divided into a plurality of strata (hereinafter referred to as layers) in the travelling direction of the beam (in the direction of a depth from a body surface of the patient 13, and each of the layers is separated into a plurality of small regions as spots before application of irradiation with the beam by way of example.

The treatment-planning unit 6 stores treatment-plan information on patients, acquired beforehand. The treatment-plan information contains irradiation data (beam-energy information, beam irradiation-position information, target dose values of the charged particle beam, against the respective irradiation-positions, and so forth), and tolerance data (information on an allowable beam position, and an allowable beam width, in the upstream beam monitor 11*a*, information on an allowable beam position, and an allowable beam width, in the downstream beam monitor 11*d*, against the respective irradiation-positions, and so forth). In the present embodiment, the treatment-planning unit 6 has a configuration for finding the irradiation data, and the tolerance data, however, the configuration may be altered such that the treatment-planning unit 6 is to find the irradiation data, and the central control unit 5 is to find the tolerance data. In this case, the treatment-planning unit 6 transmits data necessary for finding the tolerance data to the central control unit 5, and the central control unit 5 works out the tolerance data on the basis of the data received. The target dose value as the irradiation data is decided for every spot position in the respective layers.

Upon the patient 13 being fixed onto the treatment table (bed), a doctor inputs a preparation-start signal from the input device of the operation terminal 40. Upon the central control unit 5 having received the preparation-start signal, the central control unit 5 receives the treatment-plan information on a relevant patient from the treatment planning unit 6, thereby outputting bed-position information to the treatment table controller 8*a*2. The treatment table controller 8*a*2 moves the treatment table 10 such that the patient 13 is placed at a predetermined position on a line extended from a beam axis on the basis of the bed-position information, thereby completing positioning. Further, the central control unit 5 outputs gantry-angle information to the rotary gantry controller 8*a*1. The rotary gantry controller 8*a*1 rotates the rotary gantry 14 on the basis of the gantry-angle information to cause the rotary gantry 14 to be disposed at a predetermined angle. Further, the central control unit 5 transmits the target dose value of the charged particle beam, and tolerance data, for every irradiation-position, to the monitor-monitoring control unit 8*b*. The central control unit 5 works out an excitation current value necessary for exciting the scanning electromagnet 11*b* on the basis of the beam-energy information, and the irradiation-position information, contained in the irradiation data, to find an excitation current parameter, thereby transmitting the excitation current parameter to the scanning-electromagnet power-supply control unit 8*c*. Further, the central control unit 5 finds an operation parameter for an accelerated operation of the circular accelerator 16, and an operation parameter of the beam transport system 2, for transportation of the charged particle beam emitted from the circular accelerator 16 to the irradiation nozzle 11, on the basis of the treatment-plan information, thereby transmitting these operation parameters to the accelerator-transport-system controlling system 7.

Upon completion of treatment preparation, the doctor inputs a treatment-start signal from the input device of the operation terminal 40. Upon the central control unit 5 receiving the treatment-start signal, the central control unit 5 transmits a command signal to the accelerator-transport-system controlling system 7. The accelerator-transport-system controlling system 7 sets an operation parameter corresponding to the layer to be initially irradiated (initial beam-energy information) to the circular accelerator 16, and the beam transport system 2, respectively. Upon the operation parameter being set to the circular accelerator 16, and the beam transport system 2, respectively, completing the treatment preparation (Step 30), the scanning-electromagnet power-supply control unit 8c excites the scanning electromagnet 11b on the basis of the excitation current parameter (Step 31). After the scanning electromagnet 11b is energized by an excitation current corresponding to the initial irradiation spot, the dose-monitoring controller 8b3 of the monitor-monitoring control unit 8b starts monitoring the radiation exposure dose of the beam on the basis of a target dose value against a relevant spot position (Step 32), thereby completing an irradiation preparation.

Upon the central control unit 5 transmitting a beam-emission start command (Step 33), the accelerator-transport-system controlling system 7 activates the ion source, whereupon a charged particle (a proton or a heavy particle) is generated. The front-stage accelerator 15 accelerates the charged particle from the ion source, emitting the charged particle to the circular accelerator 16. The circular accelerator 16 further accelerates a charged particle beam. The charged particle beam that is revolving is accelerated up to a target energy to be emitted from the circular accelerator 16 to the beam transport system 2. The charged particle beam reaches the scanning irradiation unit 3 via the beam transport system 2. The charged particle beam travels along the beam axis inside the irradiation nozzle 11, passing through the upstream beam monitor 11a, the scanning electromagnet 11b, the dose monitor 11c, and the downstream beam monitor 11d in sequence. The charged particle beam emitted from the irradiation nozzle 11 is irradiated to an affected part of the patient 13.

The dose-monitoring controller 8b3 receives measurement data obtained by the dose-monitor 11c to be processed, thereby finding a radiation exposure dose against a relevant irradiation spot. Irradiation with the charged particle beam is continued until a radiation exposure dose against the initial irradiation spot reaches the target dose value. Upon the dose-monitoring controller 8b3 determining that the radiation exposure dose has reached the target dose value, the dose-monitoring controller 8b3 outputs an irradiation-expiration signal to the central control unit 5 (Step 34). The central control unit 5 stops the emission of the charged particle beam (Step 35).

First detection data detected by the upstream beam monitor 11a is fetched by the upstream beam monitor-monitoring controller 8b1, and second detection data detected by the downstream beam monitor 11d is fetched by the downstream beam monitor-monitoring controller 8b2, thereby finding an irradiation position of the charged particle beam, and a beam width (Step 36). If the position of the beam, and the beam width have no abnormality (if it is determined that the beam position is within the allowable beam position, and the beam width is within the allowable beam width) upon completion of the processing, there is made a determination on whether or not an irradiation spot upon irradiation-expiration is the final spot position in the layer. If it is determined that the irradiation spot is not the final irradiation spot position (If No), an operation reverts to Step 31, whereupon the scanning-electromagnet power-supply control unit 8c changes the excitation current value of the scanning electromagnet 11b so as to irradiate the next spot with the charged particle beam. Upon the scanning-electromagnet power-supply control unit 8c causing the scanning electromagnet 11b to be excited on the basis of the excitation current parameter (Step 31), the dose-monitoring controller 8b3 of the monitor-monitoring control unit 8b resumes monitoring of the beam dose on the basis of a target dose value against the next irradiation spot position (Step 32). Upon the central control unit 5 transmitting the beam-emission start signal, irradiation of the next irradiation spot position with the charged particle beam is started (Step 33). A control flow 37 from, scanning electromagnet setting (Step 31) up to a determination on whether or not the irradiation spot is the final irradiation spot position is repeatedly executed until it is determined that the irradiation spot upon the irradiation-expiration is the final spot position in the layer (until determined Yes).

Upon completion of the irradiation to all the spots, the central control unit 5 determines whether or not the layer where the irradiation is completed is the final layer against the patient 13. If the layer is not the final layer (If No), the central control unit 5 transmits the command signal to the accelerator-transport-system controlling system 7. The accelerator-transport-system controlling system 7 sets an operation parameter corresponding to the layer to be next irradiated to the circular accelerator 16, and the beam transport system 2, respectively, thereby starting the preparation for the next operation (Step 30). This control flow 38 is repeated until the irradiation of all the layers is completed. Upon the completion of the irradiation of all the spots, and all the layers, treatment completion is reached (Step 39).

Now, there is described hereinafter measurement on a beam position, and a beam width in a downstream beam monitor system according to the related art method. With the downstream beam monitor-monitoring controller according to the related art, in processing for measurement on the position of the charged particle beam, and the beam width, in FIG. 4, measurement data blocks corresponding to the number of all the channels in the downstream beam monitor are fetched, and subsequently, an offset portion of each of the channels is subtracted, thereby retrieving a peak channel. After completion of retrieval, data blocks corresponding to not more than N % (for example, 30%) of an output of the peak channel are excluded to thereby execute Gaussian-fit processing. Thereafter, the irradiation position of the charged particle beam and the beam width are worked out. Such a processing as described above has been similarly applied to the downstream beam monitor-monitoring controller according to the related art.

With the method of the related art, data blocks on all the channels are fetched for processing although the number of the channels, actually necessary for working out the position of the beam, and the beam width, is only the channels corresponding to not less than N % of the output of the peak channel, so that it has been necessary to install the pulse counters in the monitor-signal processor, and the integrated-pulses fetching devices in the downstream beam monitor controller, corresponding to the number of the channels. For this reason, there has existed a problem that if a monitor system is made up of channels more than those in the past, a larger number of those devices, to the extent of an increase in the number, must be installed.

A beam monitor system according to the present embodiment has been developed in order to solve the problem described as above. There is described hereinafter the beam monitor system according to the present embodiment.

First, a configuration of the beam monitor system is described hereinafter. The beam monitor system according to the present embodiment is provided with a beam monitor, a monitor signal processor, and a beam-monitor control unit. Herein, a configuration example of a downstream beam monitor system, as the beam monitor system, is described with reference to FIG. 3. Further, an upstream beam monitor system is similar in configuration to the downstream beam monitor system, the configuration of the upstream beam monitor system differing only in respect of the number of channels of a beam monitor. The downstream beam monitor $11d$ is connected to the downstream beam monitor-monitoring controller $8b2$ via a monitor signal processor 22.

The downstream beam monitor $11d$ is a multi-wire ion-chamber type beam monitor. The downstream beam monitor $11d$ is provided with an X-electrode for detecting a position in an x-axis direction, passed by the charged particle beam, a Y-electrode for detecting a position in a y-axis direction, passed by the charged particle beam, high-voltage electrode (a voltage-application electrode, not shown) for applying a voltage, and a current-frequency converter (pulse generator) 23. In the present embodiment, a configuration whereby the X-electrode, and the Y-electrode are disposed in this order from the upstream side in the traveling direction of the charged particle beam is described by way of example, however, a configuration whereby the Y-electrode, and the X-electrode are disposed in this order may be adopted. Each of the X-electrode and the Y-electrode is charge-collection electrode made up of tungsten wires (wire electrodes) that are strung at equal intervals. The wire electrode as a constituent of the X-electrode as well as the Y-electrode is disposed on a beam track of the charged particle beam to thereby detect the charged particle beam. Application of a voltage to the high-voltage electrode causes an electric field to be generated between the X-electrode and the Y-electrode, thereby causing an electric field to be generated between the X-electrode and the high-voltage electrode. Upon the charged particle beam passing through an ion-chamber, an gas between the high-voltage electrode and the X-electrode as well as an gas between the high-voltage electrode and the Y-electrode undergoes ionization, whereupon an ion pair is generated, and the ion pair generated is moved to the X-electrode and the Y-electrode, respectively, by the agency of the electric field to be recovered by a wire (hereinafter, referred to as a channel). Accordingly, a beam shape 21 can be measured by measuring a quantity of an electric charge detected by each of the channels. Further, a position of the center of gravity of the beam, and a beam width can be worked out by processing respective quantities of the electric charges detected by the respective channels.

The electric charge detected by each of the channels is inputted to the pulse generator 23. The pulse generator 23 converts the electric charge as received into a pulse signal, subsequently outputting the pulse signal (a detection signal) to the monitor signal processor 22. The monitor signal processor 22 is provided with a plurality of pulse counters, receiving the pulse signal as inputted to execute signal processing. More specifically, the pulse counter of the monitor signal processor 22 executes integration of pulse numbers on the basis of the pulse signal as inputted, outputting the pulse numbers as integrated to an integrated-pulses fetching device. The monitor signal processor 22 is provided with two units of the integrated-pulses fetching devices (a first integrated-pulses fetching device, and a second integrated-pulses fetching device). The first integrated-pulses fetching device is connected to the pulse counters linked to the X-electrode, collecting data blocks on the pulse numbers based on the signal detected by the X-electrode, thereby finding a beam position as well as a beam width of the charged particle beam, in the x-axis direction. The second integrated-pulses fetching device is connected to the pulse counters linked to the Y-electrode, collecting data blocks on the pulse numbers based on the signal detected by the Y-electrode, thereby finding a beam position as well as a beam width of the charged particle beam, in the y-axis direction. The first integrated-pulses fetching device, and the second integrated-pulses fetching device are each connected to a CPU inside the downstream beam monitor-monitoring controller $8b2$. Respective data blocks (processing signals) of the beam position, and the beam width, as collected, and found by the first integrated-pulses fetching device, and the second integrated-pulses fetching device, respectively, are fetched by the CPU. The CPU works out a beam shape of the charged particle beam having passed through the wire electrode, and a position of the center of gravity as well as a beam width of the beam, on the basis of the processing signals. The beam shape of the charged particle beam indicates a beam shape in a plane (X-Y plane) vertical to the beam track of the charged particle beam. The downstream beam monitor-monitoring controller $8b2$ can find a beam shape in the x-axis direction of the charged particle beam having passed through the X-electrode on the basis of the processing signal attributable to the detection signal from the X-electrode. Further, the downstream beam monitor-monitoring controller $8b2$ can also find a beam shape in the y-axis direction of the charged particle beam having passed through the Y-electrode on the basis of the processing signal attributable to the detection signal from the Y-electrode. In the present embodiment, there is adopted a configuration whereby the downstream beam monitor-monitoring controller $8b2$ finds the beam shape in the x-axis direction, and the beam shape in the y-axis direction, respectively, however, another configuration may be adopted whereby the first integrated-pulses fetching device finds the beam shape in the x-axis direction of the charged particle beam having passed through the X-electrode on the basis of the detection signal from the X-electrode, and the second integrated-pulses fetching device finds the beam shape in the y-axis direction of the charged particle beam having passed through the Y-electrode on the basis of the detection signal from the Y-electrode. In this case, the downstream beam monitor-monitoring controller $8b2$ finds the beam shape in the X-Y plane on the basis of information on the beam shape in the x-axis direction, from the first integrated-pulses fetching device, and information on the beam shape in the y-axis direction, from the second integrated-pulses fetching device.

Figure 3:
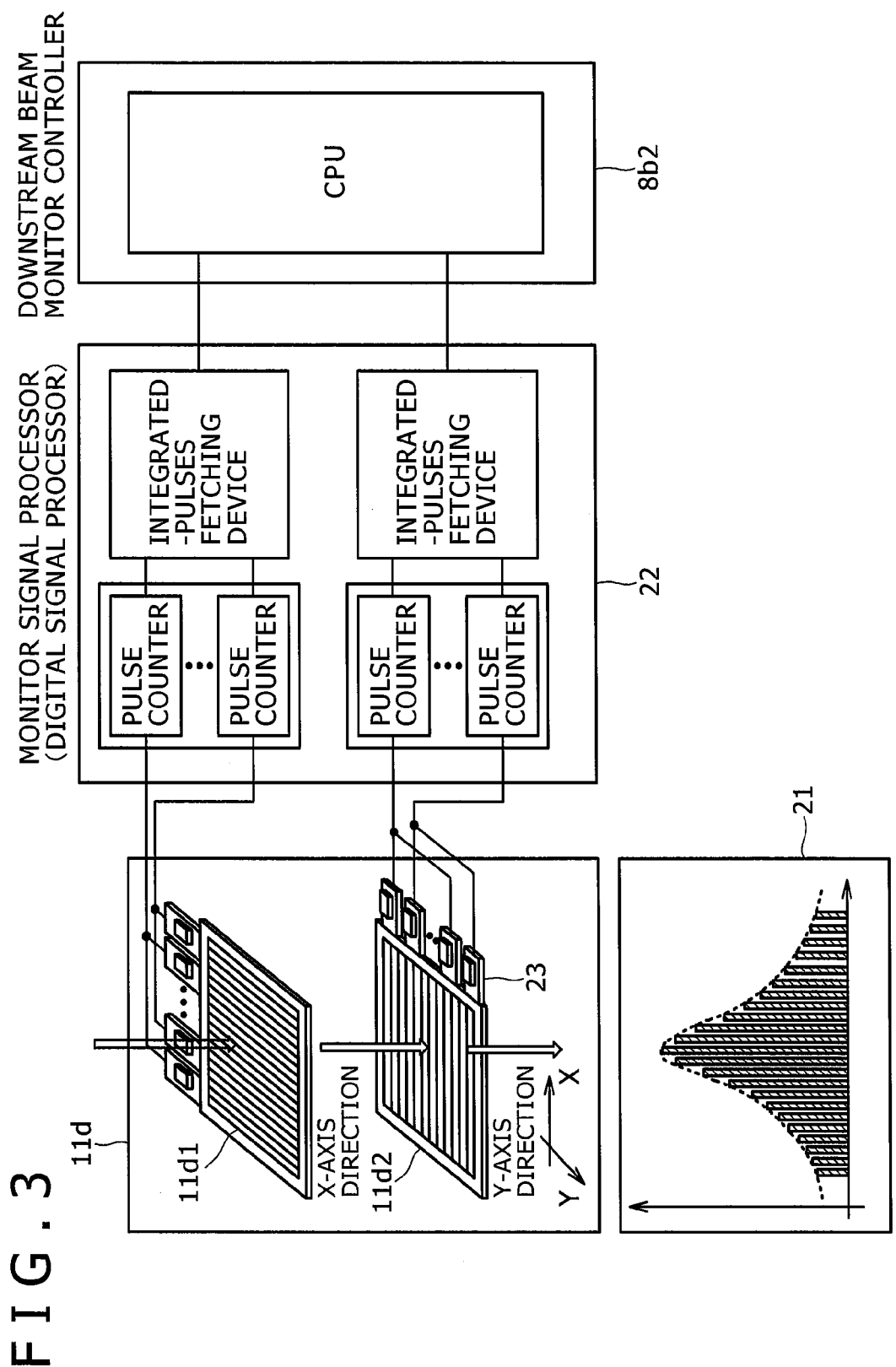
FIG. 3 is a schematic representation showing a monitor-monitoring control system relating to beam monitors of the particle beam irradiation system according to the embodiment of to the invention.

Next, referring to FIG. 5, there is described hereinafter a method for measuring a beam position, and a beam width, using the downstream beam monitor system according to the present embodiment. The downstream beam monitor $11d$ according to the present embodiment is provided with an x-axis beam monitor $11d1$ including the X-electrode, and the pulse generators 23, and a y-axis beam monitor $11d2$ including the Y-electrode, and the pulse generators 23, as shown in FIG. 3. Since a configuration between the x-axis beam monitor $11d1$ and the monitor signal processor 22 is identical to that between the y-axis beam monitor $11d2$ and the monitor signal processor 22, the x-axis beam monitor $11d1$ is described by way of example. The x-axis beam monitor 11*d*1 is comprised of, for example, 160 lengths of the wire electrodes (the X-electrode) that are strung at equal intervals, thereby having 160 channels.

First, all the channels are divided into ten segments from Segment A to Segment J by 16 channels (ch), adjacent to each other. That is, the x-axis beam monitor 11*d*1 is made up of a plurality of the segments (10 segments in the case of the present embodiment), a plurality of the wire electrodes, adjacent to each other (16 channels of the wire electrodes, in the case of the present embodiment) being organized into one segment. Thus, the one segment is made up of the plural wire electrodes adjacent to each other. In the case where the wire electrodes of the x-axis beam monitor 11*d*1 are arranged in a physical row representing respective installation positions, and are sequentially indicated as channel 1, 2, 3, 4, . . . 160, respectively, by starting from an end of the row, Segment A includes the channels 1 to 16, Segment B the channels 17 to 32, Segment C the channels 33 to 48, Segment D the channels 49 to 64, . . . Segment I the channels 129 to 144, and Segment J the channels 145 to 160. Further, with the present embodiment, two segments adjacent to each other are organized into one group. More specifically, Segments A, B are organized into Group 1, Segments C, D Group 2, Segments E, F Group 3, Segments G, H Group 4, and Segments I, J Group 5. In this case, one group is made up such that a width of the plural wire electrodes making up the one group, from one end thereof to the other, is larger than the beam width of the charged particle beam scheduled to be emitted, and a beam distribution necessary for calculation of a beam position, and a beam width is to appear in Segment {(the number of the segments in one group)−1}.

Figure 5:
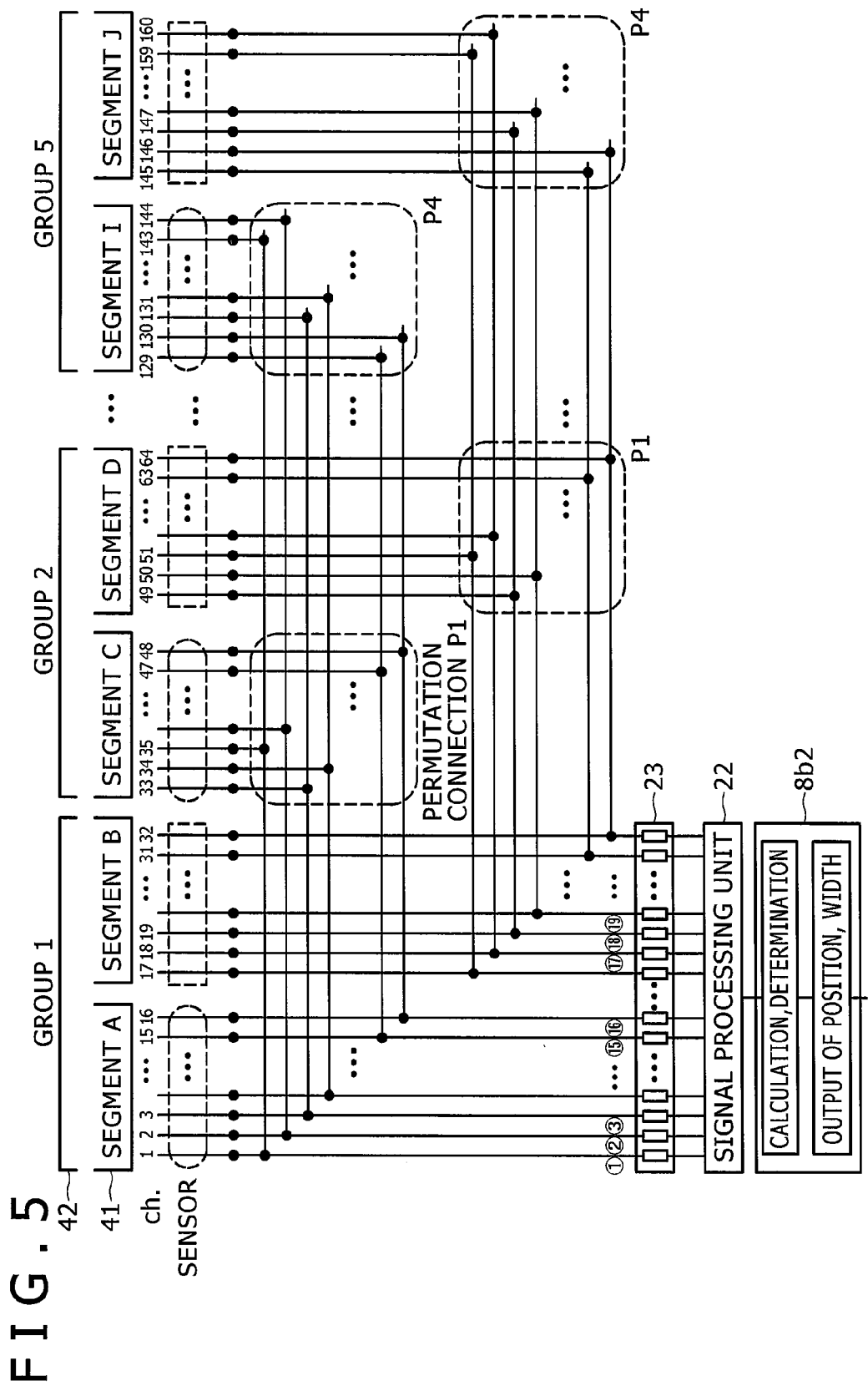
FIG. 5 is a view showing processing for grouping of channels, and connection (an example where one segment: 16 ch, one group: two segments, 5 groups in all)

In FIG. 5, the respective channels (1ch to 32ch) of Segments A, B, belonging to Group 1, are connected to the respective pulse generators 23. The x-axis beam monitor 11*d*1 is provided with a number of the pulse generators (the current-frequency converters) 23, identical in number to the number of the wire electrodes belonging to the one group. In the case of the present embodiment, 32 units of the pulse generators 23 are provided on the downstream side of the wire electrodes in the x-axis beam monitor 11*d*1. The pulse generator 23 is connected to the monitor signal processor 22. The monitor signal processor 22 includes a number of the pulse counters, identical to the number of the pulse generators 23, and two units of the integrated-pulses fetching devices. More specifically, the monitor signal processor 22 includes a number of the pulse counters, identical in number to the sum (64 units in the case of the present embodiment) of the number (32 units in the case of the present embodiment) of the wire electrodes belonging to the one group of the x-axis beam monitor 11*d*1, and the number (32 units in the case of the present embodiment) of the wire electrodes belonging to the one group of the y-axis beam monitor 11*d*2. The monitor signal processor 22 is connected to a number of the wire electrodes belonging to the one group, respectively, via interconnections identical in number thereto, such that a detection signal outputted from one of the wire electrodes, selected from the respective groups of the x-axis beam monitor 11*d*1, is inputted from the same interconnection. If the pulse generators 23 and the monitor signal processor 22 are able to process all the signals (16 ch×2) of Group 1, as described above, this is sufficient.

To describe a connection method according to the present embodiment, the wire electrodes of the respective channels belonging to one segment are connected to the monitor signal processor 22 via the same interconnection as that of the wire electrode of any one segment belonging to another group. For example, the respective wire electrodes of 33 ch to 48 ch of Segment C belonging Group 2 are connected to any one of the respective wire electrodes of 1 ch to 16 ch of Segment A belonging to Group 1. The respective wire electrodes of 65 ch to 80 ch of Segment E belonging Group 3 are connected to any one of the respective wire electrodes of 1 ch to 16 ch of Segment A belonging Group 1. The respective wire electrodes of Segment G belonging to Group 4 are connected to any one of the respective wire electrodes of 1 ch to 16 ch of Segment A belonging to Group 1. The respective wire electrodes of 129 ch to 144 ch of Segment I belonging to Group 5 are connected to any one of the respective wire electrodes of 1 ch to 16 ch of Segment A belonging to Group 1. In the same way as described above, the respective wire electrodes of Segment B belonging to Group 1 are connected to the respective wire electrodes of Segment D belonging to Group 2, the respective wire electrodes of Segment B belonging to Group 1 are connected to the respective wire electrodes of Segment F belonging to Group 3, the respective wire electrodes of Segment B belonging to Group 1 are connected to the respective wire electrodes of Segment H belonging to Group 4, and the respective wire electrodes of Segment B belonging Group 1 are connected to the respective wire electrodes of Segment J belonging to Group 5. Further, the respective channels from 33 ch to 48 ch of Segment C are connected to the respective channels from 1 ch to 16 ch of Segment A, and at this point in time, the respective channels of Segment C are connected thereto after permutation of respective connection destinations via a permutation connection P1. Further, the respective channels of Segment D in Group 2 are similarly connected to the respective channels of Segment B after permutation of respective connection destinations via the permutation connection P1. Segment E in Group 3 is connected to the respective channels of Segment A via a permutation connection P2 differing from the permutation connection P1, and the respective channels of Segment F as well are similarly connected to the respective channels of Segment B via the permutation connection P2. Segments G, H in Group 4 are connected to Segments A, B, respectively, via a permutation connection P3 differing from the permutation connections P1, P2, and Segments I, J in Group 5 are connected to Segments A, B, respectively, via a permutation connection P4 differing from the permutation connections P1, P2, and P3. Such connections are repeated until all the channels are connected to either Segment A, or Segment B, whereupon a configuration is completed. Thus, the wire electrode belonging to a segment is connected to the wire electrode belonging to a segment of another group via the permutation connection that differs on a group-by-group basis.

Figure 6:
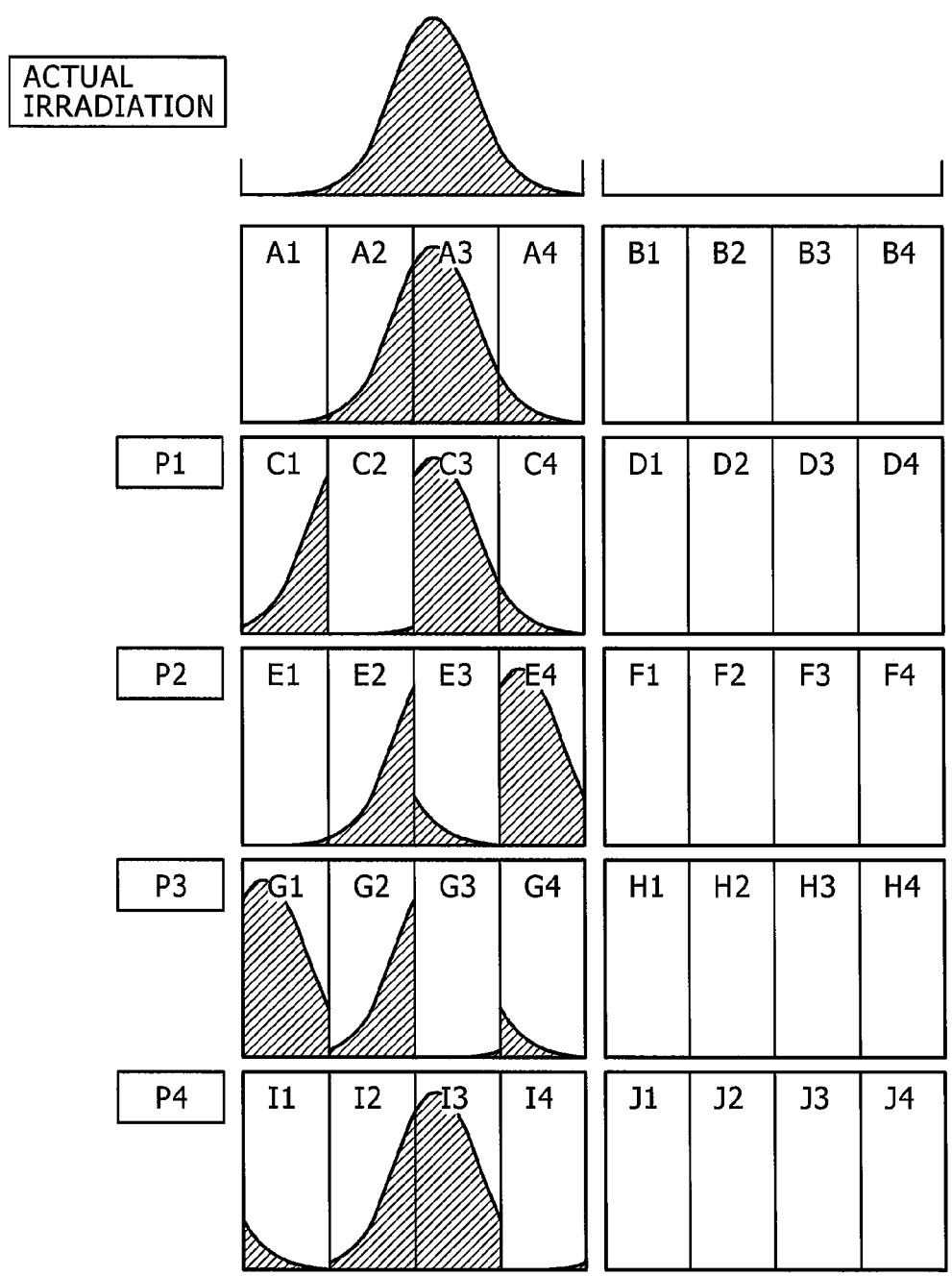
FIG. 6 is view showing output-distributions a current-frequency converter due to permutation connection using the particle beam irradiation system according to the embodiment of to the invention.

An example of the permutation connection is described hereinafter. One segment is divided into a plurality of sections (for example, divided sections A1 to A4), as shown in FIG. 6, thereby executing permutation whereby the sections are interchanged on a section-by-section basis. For example, the permutation connection P1 is a permutation whereby the section C2 is interchanged with the section C1, P2 a replacement whereby the section E3 is interchanged with the section E2, P3 a permutation whereby the section G3 is interchanged with the section G1, and P4 a permutation whereby the section 14 is interchanged with the section I1. In the present embodiment, a permutation connection is executed according to the permutation example described as above.

Next, there is described hereinafter an operation according to the present embodiment. Upon the monitor signal processor 22 receiving a detection signal from the wire electrode, the monitor signal processor 22 finds group information indicating which group's detection signal of the wire electrode a received detection signal is. Further, the monitor signal processor 22 arranges the detection signals in a different sequence on the basis of permutation connection information, thereby finding a beam shape of the charged particle beam having passed through the wire electrode. The monitor signal processor 22 transmits a processing signal containing both the group information, and beam-shape information, as found, to the CPU of the downstream beam monitor-monitoring controller 8b2. Further, a storage provided in the monitor signal processor 22 may store the detection signal received to subsequently process the detection signal stored, thereby transmitting the processing signal. The downstream beam monitor-monitoring controller 8b2 finds a beam width of the charged particle beam having passed through the wire electrode on the basis of the beam-shape information received. Further, the downstream beam monitor-monitoring controller 8b2 finds a beam position of the charged particle beam having passed through the wire electrode on the basis of both the beam-shape information, and the group information, as received. The downstream beam monitor-monitoring controller 8b2 causes both the beam position and the beam width, as found, to be displayed on the display screen provided in the operation terminal 40. A display unit displays the beam position as well as the beam width of the charged particle beam. Suppose the case where beam irradiation can be normally executed such as 50a at a normal time in FIG. 7, according to a target decided by the treatment-planning unit 6. Assuming that Segments I, J are actually irradiated with the beam, respective values detected at Segments I, J are replaced at the permutation connection P4 to be connected to Segments A, B, respectively, before being sent out to the pulse generators 23. At this point in time, an output appears like an output distribution (normal time) 51a, being unable to obtain a Gaussian distribution due to the effect of the permutation at P4. However, because where to be irradiated with the beam is pre-decided by the treatment planning unit 6, which of the permutation connections the actual irradiation beam has been applied can also be predicted on the basis of planned data. In the present embodiment, Segments I, J each are a planned target-position, so that the permutation by P4 can be predicted, and a Gaussian distribution like a reverse-permutation distribution 52a (normal time) can be obtained by execution of reverse-permutation. If, the Gaussian distribution is obtained, this will definitely indicate that the actual irradiation position is in agreement with the irradiation position according to the planned data, so that the beam position and the beam width can be accurately known. Furthermore, since the pulse generators 23 as well as the monitor signal processors 22, corresponding to the channels in one group only, are required, it is possible to realize a low-cost monitor system.

Figure 7:
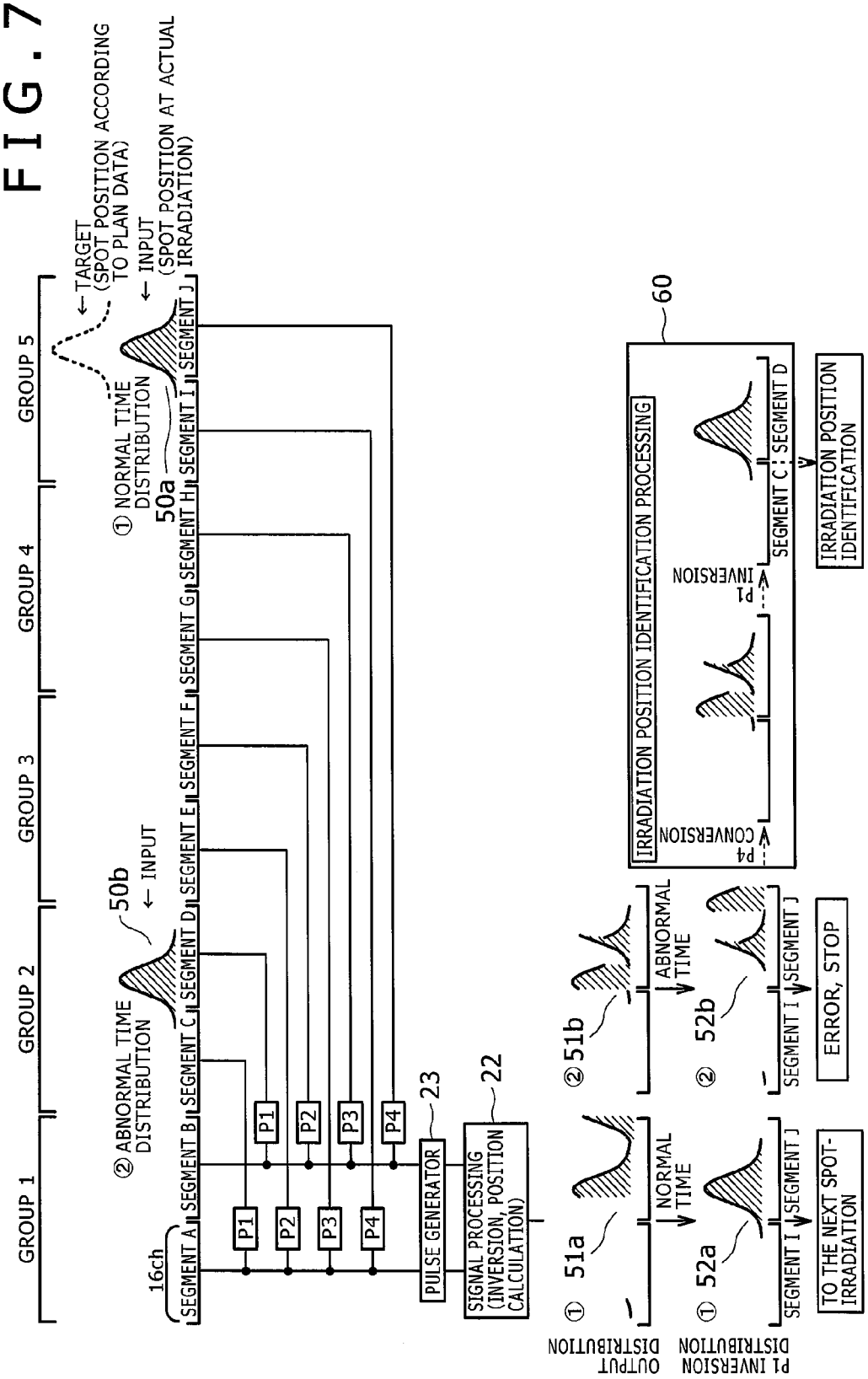
FIG. 7 is a schematic representation showing an operation in a channel-grouping monitor system using the particle beam irradiation system according to the embodiment of to the invention.

Further, suppose the case (50b at an abnormal time) where an actual beam irradiation position differs from a target irradiation position based on a treatment plan, as shown by 50b in FIG. 7. Suppose, for example, the case where the actual beam irradiation positions have turned out Segments C, D whereas the target irradiation positions are Segments I, J. In such a case, values detected at Segments C, D, respectively, are replaced by P1 to be sent out to the pulse generators 23, respectively, whereupon an output distribution 51b (abnormal time) is obtained. However, because the target irradiation positions based on the treatment plan are Segments I, J, reverse-permutation of the output is executed via P4 at the monitor signal processors 22, and as a result, a reverse-permutation output distribution 52b (abnormal time) is obtained, so that the Gaussian distribution cannot be obtained. In this case, the downstream beam monitor-monitoring controller 8b2 outputs an error signal indicating a beam error to the central control unit 5. Upon the central control unit 5 receiving the error signal, the central control unit 5 outputs a beam-stop signal to the accelerator-transport-system controlling system 7, thereby stopping the charged particle beam outgoing from the circular accelerator 16. Further, the downstream beam monitor-monitoring controller 8b2 can identify an abnormal irradiation position of the charged particle beam by execution of irradiation position identification processing 60. If the reverse-permutation via P1, and the reverse-permutation via P2 are sequentially executed against an output distribution where an abnormal irradiation has occurred, thereby identifying a reverse-permutation whereby the Gaussian distribution is obtainable, it is possible to accurately determine to which channel an abnormal irradiation has been applied. In the case of the present embodiment, the Gaussian distribution is obtained by the reverse-permutation via P1, so that it becomes definitely clear that the abnormal irradiation has been applied to a specific channel in Group 2. Further, in the case where the beam width has undergone a change, there is run a simulation considering a permutation connection against an optional beam width in a scope, and the result of the simulation is compared with an actual irradiation distribution, whereupon the beam position, and the beam width can be identified. In this simulation, an operation from a sensor in a real-world beam monitor system up to before inputting to the pulse generator is simulated on a computer, an input is given such that a beam position, and a beam width each are changed at constant intervals from a given value to a given value on the assumption that the actual irradiation distribution at the time of an abnormal irradiation is a Gaussian distribution, respective results of computer outputs with respective permutation connections dependent on the beam positions, applied thereto, are compared with an actual irradiation distribution to find agreement therebetween, thereby finding a beam position as well as a beam width at the time of the abnormal irradiation. By so doing, with the monitor system according to the present embodiment, it becomes possible to more accurately administer a radiation exposure dose against a patient.

With the particle beam irradiation system provided with the beam monitor system according to the present embodiment, the channels for use in working out the position of the charged particle beam, and the beam width are restricted, so that it is unnecessary to prepare both the amplifiers and the signal processors, corresponding in number to all the channels. A beam monitor system according to the related art is hereinafter compared with the beam monitor system according to the present embodiment. In the case of the beam monitor system according to the related art, if an x-axis beam monitor is made up of 160 lengths of wire electrodes, 160 units each of pulse generators, and pulse counters, disposed in the back-end stage thereof, are installed, the 160 units being identical in number to the number of the wire electrodes (the number of channels). If a y-axis beam monitor is made up of 160 lengths of wire electrodes, 160 units each of pulse generators, and pulse counters, disposed in the back-end stage thereof, are similarly installed. Accordingly, the monitor system according to the related art has 160 units of the pulse generators, and 160 units of the pulse counters. In contrast to the beam monitor system according to the related art, with the beam monitor system according to the present embodiment, even if the x-axis beam monitor is made up of 160 lengths of the wire electrodes, the beam position of the charged particle beam, and the beam width can be found by a configuration provided with 32 units of the pulse generators, and 32 units of the pulse counters, 32 units being sufficiently fewer than the number of the wire electrodes (the number of the channels). With the beam monitor system according to the present embodiment, the charge-collection electrode is made up of plural groups, each of the groups being made up of the plural wire electrodes adjacent to each other, and the signal processor is connected to all the wire electrodes via a number of interconnections, identical in number to the number of the wire electrodes belonging to the one group such that a detection signal outputted from one wire electrode selected from the respective groups is inputted from the same interconnection as described. Further, the signal processor has a configuration for finding the group information indicating which group's detection signal of the wire electrode a received detection signal is, thereby outputting the processing signal containing the group information to a beam monitor controller, whereupon the beam monitor controller finds the position of the charged particle beam having passed through the wire electrode, and the beam width on the basis of the processor. For this reason, a monitor system simple in configuration can be constructed. Further, with the present embodiment, the irradiation position can be accurately known by changing the wire connection method on a group-by-group basis, so that it is possible to realize a highly reliable monitor system.

The particle beam irradiation system provided with the beam monitor system according to the present embodiment is effective on a method for irradiation by scanning with a fine charged particle beam, in particular. More specifically, in order to execute irradiation with high precision, a small width beam is required, and there is a tendency that the number of wires per unit length of a multi-wire type monitor for measuring a beam profile will increase, however, wires that are concurrently irradiated with the charged particle beam represent only a part of all the wires. The beam monitor system according to the present embodiment represents a method for executing signal-processing of a number of wire signals, corresponding to only a scope concurrently irradiated with the charged particle beam, the beam monitor system having a configuration whereby other wires are connected to a number of wires, corresponding to an irradiation scope, respectively, so that low-cost, and high-reliability can be realized.

Further, with the particle beam irradiation system provided with the beam monitor system according to the present embodiment, the wire connection method is changed on the group-by-group basis, so that the irradiation position can be accurately known to thereby realize the highly reliable monitor system.

Second Embodiment

Figure 8:
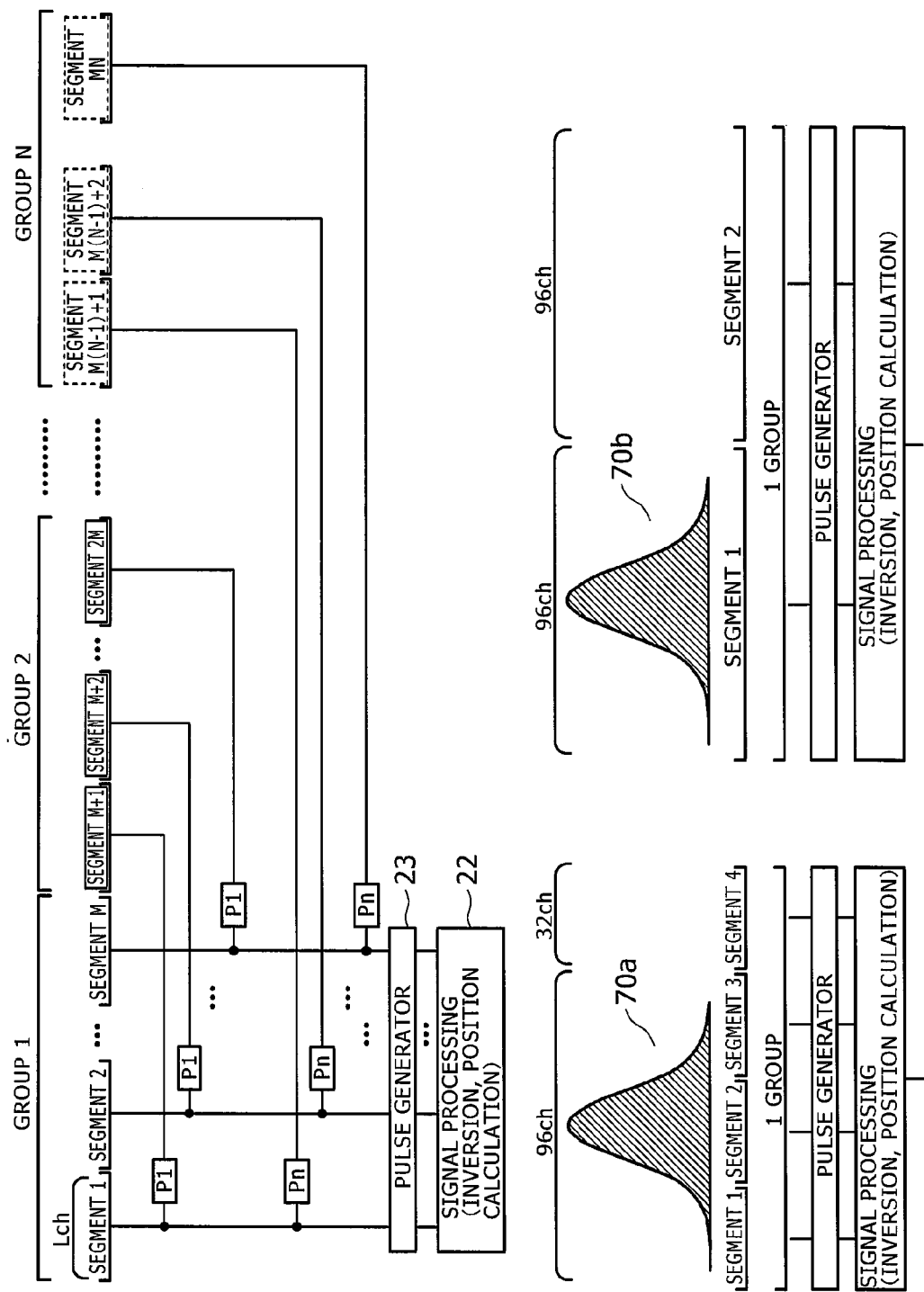
FIG. 8 is a schematic representation showing an operation in a channel-grouping monitor system using the particle beam irradiation system according to another embodiment of the invention.

There is described hereinafter a particle beam irradiation system according to another embodiment of the invention with reference to FIG. 8. With the particle beam irradiation system according to the first embodiment, the beam monitor system has the configuration whereby the two segments are organized into the one group, however, the particle beam irradiation system according to a second embodiment includes a beam monitor system whereby a plurality of segments are organized into one group. There is described hereinafter a configuration of the beam monitor system according to the present embodiment, differing from the case of the first embodiment.

The beam monitor system according to the present embodiment represents the case of a beam monitor system where group numbers are N-groups, and the number of the channels in the segment is Lch. Assuming that a beam distribution necessary for calculation of a beam position, and a beam width is to appear in (M−1) segment, the number of the segments, necessary for make up one group, is M, so that it need be only sufficient to have the pulse generator 23, and the monitor signal processor 22, capable of processing all the signals (M×L ch) in the group. If the permutation connection, and the reverse-permutation at the monitor signal processor 22 are executed according to the same procedure as in the case of the first embodiment, this will enable the beam position, the beam width, and identification of the irradiation position at the time of erroneous irradiation to be accurately known in a way similar to the case of the first embodiment.

Comparison of the present embodiment with the first embodiment is described by use of specific numerical values. If a beam distribution necessary for calculation of a beam position and a beam width corresponds to, for example, 96 ch, the number of the channels for one segment in the case of the first embodiment will be 96 ch, so that 192 ch is required to make up the one group, as shown by 70*b*. In the case of the present embodiment, if the number of channels for one segment is 32 ch, one group is made up of four segments, as shown by 70*a*, and 128 ch are required of the one group. In this case of the present embodiment, the number of the channels necessary to make up the one group can be reduced as compared with the case of the first embodiment, so that it is possible to construct a beam monitor system still lower in cost.

With the particle beam irradiation system according to the present embodiment, the channels for use in working out the position of the charged particle beam, and the beam width are restricted, so that it is possible to construct a monitor system simple in configuration as compared with the monitor system made up of both the amplifiers and the signal processors, corresponding in number to all the channels. Further, with the present embodiment, the irradiation position can be accurately known by changing the wire connection method on the group-by-group basis, so that it is possible to realize a highly reliable monitor system.

The particle beam irradiation system provided with the beam monitor system according to the present embodiment is effective on the method for irradiation by scanning with the use of a fine charged particle beam, in particular. More specifically, in order to execute irradiation with high precision, a small width beam is required, and there is a tendency that a multi-wire type monitor for measuring a beam profile will increase in the number of wires per unit length, however, wires that are concurrently irradiated with the charged particle beam represent only a part of all the wires. The particle beam irradiation system provided with the beam monitor system according to the present embodiment has a configuration whereby other wires are connected to a number of wires, corresponding to an irradiation scope, respectively, adopting a method for executing signal-processing of a number of signals, corresponding to only a scope concurrently irradiated with the charged particle beam, so that low-cost, and high-reliability can be realized.

With the particle beam irradiation system provided with the beam monitor system according to the present embodiment, the wire connection method is changed on the group-by-group basis, so that the irradiation position can be accurately known to thereby realize the highly reliable monitor system.

Third Embodiment

There is described hereinafter a particle beam irradiation system according to a third embodiment of the invention with reference to FIG. 9. In contrast to the first embodiment relating to the particle beam irradiation system provided with the beam monitor system for monitoring the beam position, and the beam width in execution of the spot-scanning irradiation method, the particle beam irradiation system according to the present embodiment is provided with a beam monitor system for monitoring a beam position, and a beam width in execution of a raster scanning irradiation method. The particle beam irradiation system according to the present embodiment is provided with the beam monitor system for monitoring the beam position, and the beam width in execution of the raster scanning irradiation method whereby an affected part of a patient 13 is divided into a plurality of layers in the travelling direction of the charged particle beam, thereby scanning with the charged particle beam while continuing irradiation of respective layers with the charged particle beam (the beam remaining ON). There is described hereinafter a configuration of the beam monitor system according to the present embodiment, differing from that of the first embodiment.

Upon completion of treatment preparation, doctor inputs a treatment-start signal from the input device of the operation terminal 40. Upon the central control unit 5 receiving the treatment-start signal, the central control unit 5 transmits the command signal to the accelerator-transport-system controlling system 7. The accelerator-transport-system controlling system 7 sets an operation parameter corresponding to the layer to be initially irradiated (initial-irradiation beam-energy information) to the circular accelerator 16, and the beam transport system 2, respectively. Upon the operation parameter being set to the circular accelerator 16, and the beam transport system 2, respectively, thereby completing the treatment preparation (Step 30), the scanning-electromagnet power-supply control unit 8c excites the scanning electromagnet 11b on the basis of the excitation current parameter (Step 31a). After the scanning electromagnet 11b is excited by the excitation current corresponding to the initial irradiation spot, the dose-monitoring controller 8b3 of the monitor-monitoring control unit 8b starts monitoring of the radiation exposure dose of the beam on the basis of the target dose value against the relevant spot position (Step 32a), thereby completing the irradiation preparation.

Upon the central control unit 5 transmitting the beam-emission start command (Step 33), the accelerator-transport-system controlling system 7 activates the ion source, whereupon the charged particle (the proton or the heavy particle) is generated. The front-stage accelerator 15 accelerates the charged particle from the ion source, emitting a charged particle beam to the circular accelerator 16. The circular accelerator 16 further accelerates the charged particle beam. The charged particle beam that is revolving is accelerated up to the target energy to be emitted from the circular accelerator 16 to the beam transport system 2. The charged particle beam reaches the scanning irradiation unit 3 via the beam transport system 2. Further, the charged particle beam travels along the beam axis inside the irradiation nozzle 11, passing through the upstream beam monitor 11a, the scanning electromagnet 11b, the dose monitor 11c, and the downstream beam monitor 11d in sequence. The charged particle beam emitted from the irradiation nozzle 11 is irradiated to the affected part of the patient 13.

The dose-monitoring controller 8b3 receives the measurement data obtained by the dose-monitor 11c to be processed, thereby finding the radiation exposure dose against the relevant irradiation spot. Irradiation with the charged particle beam is continued until the radiation exposure dose against the initial irradiation spot reaches the target dose value. Upon the dose-monitoring controller 8b3 determining that the radiation exposure dose has reached the target dose value, the dose-monitoring controller 8b3 outputs the irradiation-expiration signal to the central control unit 5 (Step 34).

The first detection data detected by the upstream beam monitor 11a is fetched by the upstream beam monitor-monitoring controller 8b1, and the second detection data detected by the downstream beam monitor 11d is fetched by the downstream beam monitor-monitoring controller 8b2, thereby finding the irradiation position of the charged particle beam, and the beam width (Step 35a). If the position of the beam, and the beam width has no abnormality (If it is determined that the beam position is within the allowable beam position, and the beam width is within the allowable beam width) upon completion of the processing, there is made a determination on whether or not the irradiation spot after irradiation-expiration is the final spot position in the layer. If it is determined that the irradiation spot is not the final irradiation spot position (If No), the scanning-electromagnet power-supply control unit 8c executes setting of a spot scanning-electromagnet on the basis of the excitation current parameter (Step 35b), the monitor-monitoring control unit 8b executes setting of a spot-dose target value (Step 35c). An operation reverts to Step 34, and a control flow 37a from the step (Step 34) for determination on the dose-expiration up to determination that an irradiation spot is the final spot position is repeatedly executed until it is determined that the irradiation spot upon the irradiation-expiration is the final spot position in the layer (until determined Yes).

Upon completion of the irradiation of all the spots in the layer, the central control unit 5 determines whether or not the layer upon completion of irradiation is the final layer of the patient 13. If the layer is not the final layer (If No), the central control unit 5 transmits the command signal to the accelerator-transport-system controlling system 7. The accelerator-transport-system controlling system 7 sets an operation parameter corresponding to the layer to be next irradiated to the circular accelerator 16, and the beam transport system 2, respectively, thereby starting preparation for the next operation (Step 30). This control flow 38a is repeated until the irradiation of all the layers is completed. Upon the completion of the irradiation of all the spots, and all the layers, treatment completion is reached (Step 39).

Thus, with the particle beam irradiation system according to the present embodiment, there is implemented the raster scanning irradiation method whereby the irradiation position is changed with the charged particle beam kept in an emitted state, thereby applying beam irradiation to the affected part.

Further, the particle beam irradiation system according to the present embodiment can be applied to the particle beam irradiation system provided with the beam monitor system according to the second embodiment, for monitoring the beam position, and the beam width.

With the particle beam irradiation system provided with the beam monitor system according to the present embodiment, the channels for use in working out the position of the charged particle beam, and the beam width are, restricted, so that it is unnecessary to prepare both the amplifiers and the signal processors, corresponding in number to all the channels. Therefore, a monitor system simple in configuration can be constructed. Further, with the present embodiment, the irradiation position can be accurately known by changing the wire connection method on the group-by-group basis, so that it is possible to realize a highly reliable monitor system.

The particle beam irradiation system provided with the beam monitor system according to the present embodiment is effective on the method for irradiation by scanning with the fine charged particle beam, in particular. More specifically, in order to execute irradiation with high precision, the small width beam is required, and there is the tendency that the multi-wire type monitor for measuring the beam profile will increase in the number of wires per unit length, however, the wires that are concurrently irradiated with the charged particle beam represent only the part of all the wires. The beam monitor system according to the present embodiment represents the method for executing signal-processing of a number of wire signals, corresponding to only the scope concurrently irradiated with the charged particle beam, the beam monitor system having the configuration whereby other wires are connected to a number of wires, corresponding to the irradiation scope, respectively, so that low-cost, and high-reliability can be realized.

Further, with the particle beam irradiation system provided with the beam monitor system according to the present embodiment, the wire connection method is changed on the group-by-group basis, so that the irradiation position can be accurately known, and a highly reliable monitor system can be realized.

Now, it is to be pointed out that the invention be not limited to any of the details of description concerning the first, second, and third embodiments, respectively, and that various modifications may be made in the invention. For example, the first, second, and third embodiments each are described in detail for explanation with greater ease, however, the invention is not necessarily limited to any of the embodiments provided with all the configurations described. For example, in the embodiment, a signal processor is comprised of the current-frequency converters, and the digital signal processor including the pulse counters, however, the signal processor may be comprised of a circuit for integrating charges to be converted into a voltage to be outputted, and an analog monitor signal processor. Further, a monitor can include any suitable number of channels, segments, and groups, and permutation connections in a group may not be identical to each other. Further, as for permutation connection, one segment is divided into a plurality of segments, and subsequently, permutation is executed through interchange between the segments. However, the permutation is not limited thereto, and can be executed by any suitable method.

What is claimed is:

1. A beam monitor system comprising:
   a collection electrode, including a plurality of wire electrodes, to detect a charged particle beam passing therethrough;
   a signal processor to receive respective detection signals outputted from the wire electrodes to execute signal processing; and
   a beam monitoring control unit to find a position as well as a beam width of the charged particle beam having passed through the wire electrode on the basis of processing signals from the signal processor,
   wherein the charge-collection electrode is made up of plural groups, each of the groups being made up of the plural wire electrodes adjacent to each other,
   wherein the signal processor is connected to all the wire electrodes via a number of interconnections, identical in number to the number of the wire electrodes belonging to the one group such that a detection signal outputted from one of the wire electrodes, selected from the respective groups, is inputted from interconnections identical to each other, and
   wherein the signal processor finds the group information indicating which group's detection signal of the wire electrode a received detection signal is, thereby outputting the processing signal containing the group information to the beam monitoring control unit.

2. The beam monitor system according to claim 1, wherein the group is divided into a plurality of segments, each of the segments being made up of the plural wire electrodes adjacent to each other, the respective wire electrodes belonging to one of the segments are connected to any one of the wire electrodes of the segment belonging to another group for connection with the signal processor via interconnections identical to each other, the wire electrode belonging to the one of the segments is connected to one of the wire electrodes of the segment belonging to other groups via a permutation connection differing on a group-by-group basis, and the signal processor arranges the respective detection signals outputted from the wire electrodes in a different sequence on the basis of permutation connection information according to planned beam irradiation-position information, thereby finding a beam position as well as a beam width of the charged particle beam.

3. The beam monitor system according to claim 2, wherein the collection electrode is made up such that a width of the plural wire electrodes making up one of the groups is larger than the width of the charged particle beam scheduled to be emitted.

4. The beam monitor system according to claim 2, wherein the one group contains a segment larger than a number of the segments, for sufficiently covering the beam width of the charged particle beam.

5. The beam monitor system according to claim 4, further comprising a display unit for receiving information on a beam position as well as a beam width, found by the beam monitoring control unit, to be displayed on a screen.

6. The beam monitor system according to claim 4, wherein beam profile information obtained by calculating a signal of a charged particle beam of an assumed beam profile by simulating a signal processing configuration of the monitor system is compared with beam profile information on the charged particle beam at the time of an abnormal irradiation, thereby finding a beam position as well as a beam width of the charged particle beam.

7. The beam monitor system according to claim 2, further comprising a display unit for receiving information on a beam position as well as a beam width, found by the beam monitoring control unit, to be displayed on a screen.

8. The beam monitor system according to claim 2, wherein the signal processor comprises a storage for storing the detection signal from the wire electrode, and processing the detection signal stored in the storage, thereby outputting the processing signal.

9. The beam monitor system according to claim 2, wherein beam profile information obtained by calculating a signal of a charged particle beam of an assumed beam profile by simulating a signal processing configuration of the monitor system is compared with beam profile information on the charged particle beam at the time of an abnormal irradiation, thereby finding a beam position as well as a beam width of the charged particle beam.

10. A charged particle beam irradiation system comprising a beam monitor system according to claim 2.

11. The beam monitor system according to claim 1, wherein the collection electrode is made up such that a width of the plural wire electrodes making up one of the groups is larger than the width of the charged particle beam scheduled to be emitted.

12. A charged particle beam irradiation system comprising a beam monitor system according to claim 11.

13. The beam monitor system according to claim 11, wherein the one group contains a segment larger than a number of the segments, for sufficiently covering the beam width of the charged particle beam.

14. The beam monitor system according to claim 11, further comprising a display unit for receiving information on a beam position as well as a beam width, found by the beam monitoring control unit, to be displayed on a screen.

15. The beam monitor system according to claim 11, wherein the signal processor comprises a storage for storing the detection signal from the wire electrode, and processing the detection signal stored in the storage, thereby outputting the processing signal.

16. The beam monitor system according to claim 11, wherein beam profile information obtained by calculating a signal of a charged particle beam of an assumed beam profile by simulating a signal processing configuration of the monitor system is compared with beam profile information on the charged particle beam at the time of an abnormal irradiation, thereby finding a beam position as well as abeam width of the charged particle beam.

17. The beam monitor system according to claim 1, further comprising a display unit for receiving information on a beam position as well as a beam width, found by the beam monitoring control unit, to be displayed on a screen.

18. The beam monitor system according to claim 17, further comprising a display unit for receiving information on a beam position as well as a beam width, found by the beam monitoring control unit, to be displayed on a screen.

19. The beam monitor system according to claim 1, wherein the signal processor comprises a storage for storing the detection signal from the wire electrode, and processing the detection signal stored in the storage, thereby outputting the processing signal.

20. A charged particle beam irradiation system comprising a beam monitor system according to claim 1.

\* \* \* \* \*